(12) United States Patent  
Chang et al.

(10) Patent No.: US 8,431,708 B2
(45) Date of Patent: *Apr. 30, 2013

(54) FLUORESCENT CARBAZOLE COMPOUNDS FOR CANCER DIAGNOSIS

(75) Inventors: Ta-Chau Chang, Taipei (TW); Chih-Chien Cho, Taipei County (TW); Cheng-Chung Chang, Taichung (TW); Chi-Chih Kang, Tainan County (TW); Zi-Fu Wang, Taipei County (TW)

(73) Assignee: Academia Sinica, Taipei (TW)

( * ) Notice: Subject to any disclaimer, the term of this patent is extended or adjusted under 35 U.S.C. 154(b) by 610 days.

This patent is subject to a terminal disclaimer.

(21) Appl. No.: 12/613,770

(22) Filed: Nov. 6, 2009

(65) Prior Publication Data

US 2011/0111429 A1    May 12, 2011

(51) Int. Cl.
    *C07D 209/82* (2006.01)
    *A61K 31/454* (2006.01)

(52) U.S. Cl.
    USPC ......... 546/193; 514/252.1; 514/277; 514/318

(58) Field of Classification Search .................. 546/193; 514/252.1, 277, 318
    See application file for complete search history.

(56) References Cited

U.S. PATENT DOCUMENTS

| | | | |
|---|---|---|---|
| 6,979,738 B2 | 12/2005 | Chang et al. | |
| 7,691,624 B2 * | 4/2010 | Chang et al. | 435/288.7 |
| 2005/0090671 A1 | 4/2005 | Chang et al. | |
| 2005/0249669 A1 | 11/2005 | Chang et al. | |
| 2007/0098233 A1 | 5/2007 | Chang et al. | |

OTHER PUBLICATIONS

Tsai Yu-Lin et al, 2007, Effect of different electronic properties on 9-aryl-substituted BMVC derivatives for new fluorecence probes.*

Liao et al., "Improved diagnostic accuracy of malignant neck lumps by a simple BMVC staining assay," Analyst, 134:708-711 (2009).
Chang et al., "A Novel Carbazole Derivative, BMVC: A Potential Antitumor Agent and Fluorescence Marker of Cancer Cells," Chemistry & Biodiversity, 1:1377-1384 (2004).
Kang et al., "Simple Method in Diagnosing Cancer Cells by a Novel Fluorescence Probe BMVC," Journal of the Chinese Chemical Society, 52:1069-1072 (2005).
Urano et al., "Selective Molecular Imaging of Viable Cancer Cells with pH-Activatable Fluorescence Probes," Nature Medicine, 15(1):104-109 (2009).
Chang et al., "A Fluorescent Carbazole Derivative: High Sensitivity for Quadruplex DNA," Anal. Chem. 75:6177-6183 (2003).
Kang et al., "A Handheld Device for Potential Point-of-Care Screening of Cancer," Analyst, 132:745-749 (2007).
Zhou et al. "Crystal Structure, Optical Properties and Theoretical Calculation of Novel Two-Photon Polymerization Initiators" Chemical Physics, 322(3):459-470 (2006).
European Search Report, Jan. 2011.

* cited by examiner

*Primary Examiner* — Rita Desai
(74) *Attorney, Agent, or Firm* — Occhiuti Rohlicek & Tsao LLP

(57) ABSTRACT

A compound of formula (I):

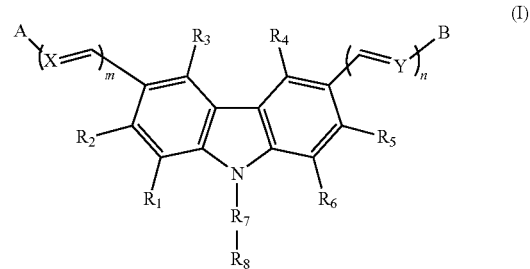

in which $R_1$-$R_8$, A, B, X, Y, m, and n are as defined herein. Also disclosed is a method for detecting a cancer cell using a compound of formula I.

22 Claims, No Drawings

```
                        SEQUENCE LISTING

<160> NUMBER OF SEQ ID NOS: 1

<210> SEQ ID NO 1
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 1
gcgcaattgc gc                                                    12
```

FLUORESCENT CARBAZOLE COMPOUNDS FOR CANCER DIAGNOSIS

BACKGROUND

Cancer is a disease characterized by deregulated proliferation of transformed cells, which infiltrate and destroy normal body tissue. Despite substantial progress in the development of cancer therapy, cancer remains a major cause of death.

It has been found that early diagnosis of cancer significantly improves the efficacy of cancer therapy, thereby reducing mortality of cancer patients. Thus, it is of great importance to identify agents useful in rapid and accurate diagnostic methods for detecting cancer at an early stage.

SUMMARY

The present invention is based on an unexpected discovery that, upon interaction with DNA, certain carbazole compounds exhibit a significantly higher fluorescence in cancer cells, particularly in their nuclei and mitochondria, as compared to normal cells.

Thus, in one aspect, this invention relates to a group of carbazole compounds that have the following formula (I):

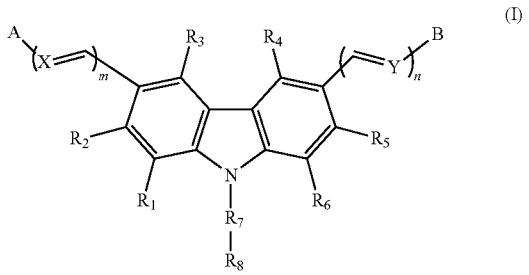

in which each of A and B, independently, is heteroaryl containing at least one nitrogen atom, each of X and Y, independently, is CH or N, each of $R_1$-$R_6$, independently, is H, $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, aryl, heteroaryl, hydroxy, $C_1$-$C_6$ alkoxy, aryloxy, heteroaryloxy, amino, $C_1$-$C_6$ alkylamino, $C_1$-$C_6$ dialkylamino, arylamino, diarylamino, thio, or halogen, $R_7$ is $C_1$-$C_{16}$ alkyl, $C_2$-$C_{16}$ alkenyl, $C_2$-$C_{16}$ alkynyl, $C_3$-$C_8$ cycloalkyl, $C_3$-$C_8$ heterocycloalkyl, aryl, heteroaryl, —$C_2H_4$—$(ZC_2H_4)_v$—, Z being O, S, or Se and v being is 1, 2, or 3, $R_8$ is $C_3$-$C_8$ heterocycloalkyl containing a nitrogen atom, $C_3$-$C_8$ heterocycloalkyl substituted by an amino group, $C_3$-$C_8$ cycloalkyl substituted by an amino group, aryl substituted by an amino group, heteroaryl containing a nitrogen atom, or $NR^aR^b$, in which each of $R^a$ and $R^b$, independently, is H, $C_1$-$C_8$ alkyl, or $R^a$ and $R^b$ form together with the nitrogen atom they are attached to a 3 to 8-membered ring, and each of m and n, independently, is 1, 2, or 3.

Referring to this formula, the compounds can have one or more of the following features. Each of A and B, independently, is heteroaryl containing one or two nitrogen atoms (e.g., pyridyl or pyrimidinyl). Examples of A and B include, but are not limited to, pyridyl substituted with alkyl (e.g., 1-methyl-pyridinium-4-yl). Each of m and n is 1. Each of $R_1$-$R_6$ is H. Each of X and Y is CH. $R_7$ is $C_8$-$C_{12}$ alkyl, $C_8$-$C_{12}$ alkenyl, $C_8$-$C_{12}$ alkynyl, or —$C_2H_4$—$(OC_2H_4)_3$—. $R_8$ is a heterocycloalkyl containing a nitrogen atom, which can be positively charged. Examples of $R_8$ include, but are not limited to, heterocycloalkyl containing a nitrogen atom (e.g., 1-methyl-piperidinium-1-yl).

The term "alkyl" refers to a straight or branched hydrocarbon. Examples of alkyl include, but are not limited to, methyl, ethyl, n-propyl, i-propyl, n-butyl, i-butyl, and t-butyl. The term "alkenyl" refers to a straight or branched hydrocarbon and one or more double bonds. Examples of alkenyl include, but are not limited to, ethenyl, propenyl, allyl, and 1,4-butadienyl. The term "alkynyl" refers to a straight or branched hydrocarbon and one or more triple bonds. Examples of alkynyl include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, iso-butoxy, sec-butoxy, and tert-butoxy.

The term "cycloalkyl" refers to a saturated hydrocarbon ring system having 3 to 8 carbon atoms. Examples of cycloalkyl include, but are not limited to, cyclopropyl, cyclobutyl, cyclopentyl, cyclohexyl, cycloheptyl, and cyclooctyl. The term "heterocycloalkyl" refers to a saturated cyclic moiety having one or more heteroatoms (such as O, N, S, or Se). Examples of heterocycloalkyl groups include, but are not limited to, piperazinyl, pyrrolidinyl, dioxanyl, morpholinyl, and tetrahydrofuranyl.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "aryloxy" refers to an —O-aryl radical. Examples of aryloxy include, but are not limited to, phenoxy. The term "heteroaryl" refers to an aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroaryloxy" refers to an —O-heteroaryl radical. Examples of heteroaryloxy include, but are not limited to, 4-pyridinoxy.

Alkyl, alkenyl, alkynyl, cycloalkyl, heterocycloalkyl, aryl, heteroaryl, alkoxy, aryloxy, and heteroaryloxy mentioned herein include both substituted and unsubstituted moieties. Examples of substituents include, but are not limited to, halogen, hydroxy, amino, cyano, nitro, thio, alkoxycarbonyl, amido, alkanesulfonyl, alkylcarbonyl, carbamido, carbamoyl, carboxy, thioureido, thiocyanato, sulfonamido, alkyl, alkenyl, alkynyl, alkyloxy, aryl, heteroaryl, cycloalkyl, and heterocycloalkyl. Cycloalkyl and heterocycloalkyl can also be fused with aryl or heteroaryl.

Shown in the table below are 7 exemplary compounds of this invention:

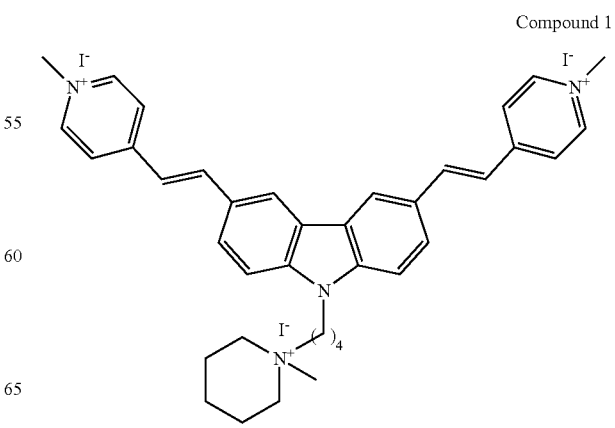

Compound 1

Compound 2
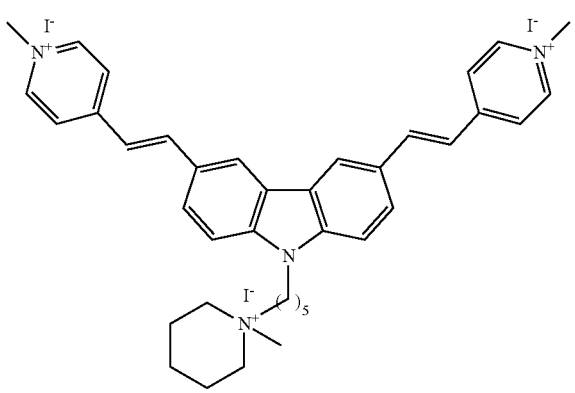

Compound 3
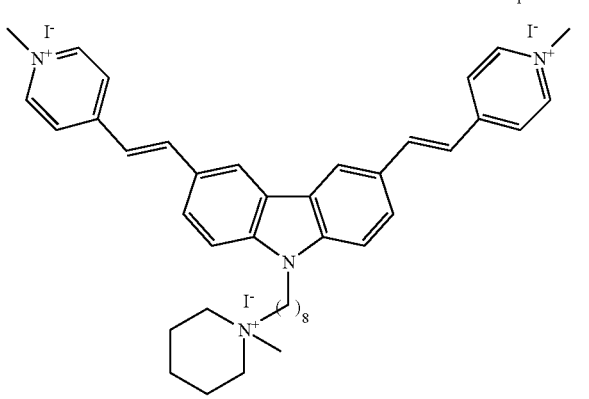

Compound 4
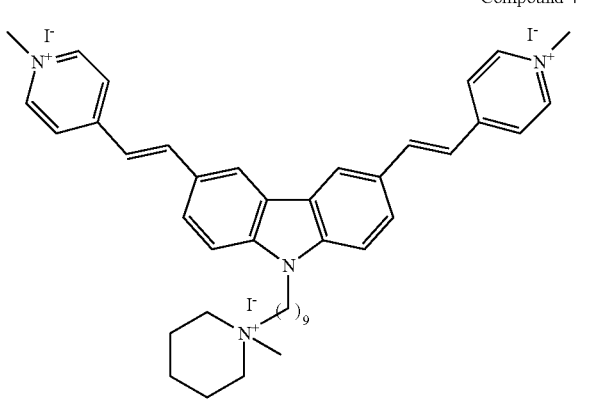

Compound 5
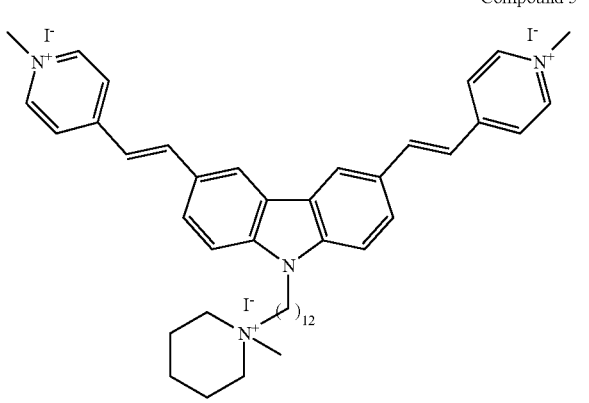

Compound 6
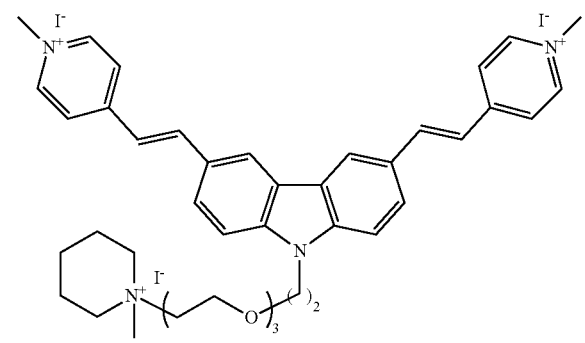

Compound 7
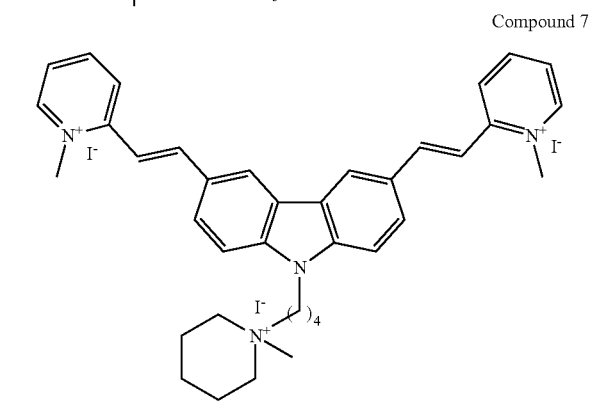

The carbazole compounds described above include the compounds themselves, as well as their salts and their pro-drugs, if applicable. A salt, for example, can be formed between an anion and a positively charged group (e.g., ammonium) on a carbazole compound. Suitable anions include chloride, bromide, iodide, sulfate, sulfite, perchlorate, hexafluorophosphate, nitrate, phosphate, citrate, methanesulfonate, trifluoroacetate, and acetate. Likewise, a salt can also be formed between a cation and a negatively charged group (e.g., carboxylate) on a carbazole compound. Suitable cations include sodium ion, potassium ion, magnesium ion, calcium ion, and an ammonium cation such as tetramethylammonium ion.

In another aspect, this invention relates to a method for detecting cancer cells, derived from either cultured cells or patient samples. The method includes (1) contacting a plurality of cells in a sample with a compound of the formula shown above, (2) detecting the fluorescence emitted from the cells, and (3) determining whether the sample contains cancer cells. If the fluorescent intensity of the sample is greater than the one obtained from non-cancer cells, the sample contains cancer cells.

The details of one or more embodiments of the invention are set forth in the accompanying drawings and the description below. Other features, objects, and advantages of the invention will be apparent from the description and from the claims.

DETAILED DESCRIPTION

We discovered that certain carbazole compounds having a positively charged N-containing group attached to position 9 of the carbazole moiety via a linker unexpectedly interacted with both nuclear and mitochondrial DNAs at a much higher level in cancer cells than in normal cells. As a result, these compounds displayed enhanced fluorescence in cancer cells as compared to their fluorescence in normal cells.

Accordingly, described herein is a group of carbazole compounds represented by formula I shown above, all of which contain a positively charged N-containing group attached to position 9 (i.e., $R_8$). These compounds also contain a linker (i.e., $R_7$) having up to 16 carbons. This linker, either alone or together with other substituents, modulates the lipophilicity/hydrophilicity of the carbazole compounds.

To synthesize these compounds, one can use synthetic chemistry transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Scheme 1 below depicts an exemplary synthesis of Compounds 1-7 mentioned above.

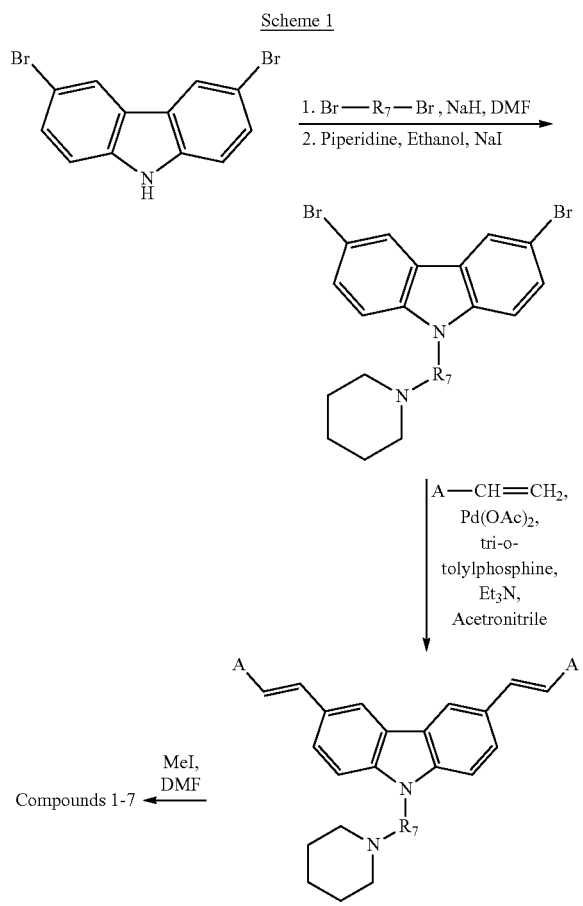

Scheme 1

Scheme 1 shows a synthetic route to 3,6,9-tri-substituted carbazole compounds, in which 3,6-dibromocarbazole is used as a starting material. The substituent at position 9 can be introduced by a standard substitution reaction and modifications of positions 3 and 6 can be achieved by well-known coupling reactions, e.g., Heck or Stille reaction. N-alkylation or protonation of the nitrogen containing moieties leads to the desired compounds 1-7.

Details of synthesis of Compounds 1-7 are described in Examples 1-7, respectively.

A carbazole compound thus synthesized can be further purified by flash column chromatography, high performance liquid chromatography, crystallization, or any other suitable methods.

Note that the carbazole compounds contain at least two double bonds, and may further contain one or more asymmetric centers. Thus, they can occur as racemates and racemic mixtures, single enantiomers, individual diastereoisomers, diastereoisomeric mixtures, and cis- or trans- or E- or Z-double bond isomeric forms. All such isomeric forms are contemplated.

Also within the scope of this invention is a method for detecting cancer cells in a sample by contacting cells in the sample with one of the carbazole compounds described above and detecting the fluorescence emitted by the cells upon irradiation with an excitation light. If the fluorescent intensity of the cells is greater than the one obtained from non-cancer cells, it is determined that the sample contains cancer cells. This method is highly sensitive and can be used to detect a single cancer cell.

Suitable in vitro assays can be used to preliminary evaluate the efficacy of the carbazole compounds of this invention in differentiating cancer cells from normal cells. (See e.g., Example 9 below).

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

Preparation of Compound 1

Under a nitrogen atmosphere, sodium hydride (0.3 g, 12.5 mmol, Aldrich) was added to a solution of 3,6-dibromo-9H-carbazole (2 g, 6.1 mmol, Aldrich) in DMF (10 ml). The mixture was stirred for 5 min, 1,4-dibromobutane (3.9 g, 18 mmol, Aldrich) was added, and the mixture was refluxed for 12 h. Flash chromatography (N-hexane/ethyl acetate 2:1) gave 3,6-dibromo-9-(1-bromobutyl)carbazole (yield: 65%). A solution of the obtained compound (1.84 g, 4 mmol) and piperidine (0.68 g, 8 mmol, Aldrich) in ethanol (30 ml) was refluxed in the presence of a trace of NaI for 24 h. The product of the reaction was purified by column chromatography (n-Hexane/ethyl acetate 1:2) and added into a high pressure flask containing a mixture of palladium(II) acetate (0.005 g, 0.02 mmol, Aldrich) and tri-o-tolylphosphine (0.04 g, 0.13 mmol, Aldrich). After addition of triethylamine (5 ml), acetonitrile (10 ml), and 4-vinylpyridine (0.53 g, 5 mmol, Aldrich), the flask was sealed, nitrogen was bubbled for 5 min, and the reaction was kept at ~105° C. for 48 h. The precipitate was collected, extracted twice with $H_2O$ and $CH_2Cl_2$, dried over anhydrous $MgSO_4$, dissolved in THF, filtered, and the product was recrystallized from acetone. A solution of this product (0.5 g, 1 mmol) in DMF (10 ml) was refluxed with an excess of $CH_3I$ for 6 h, and the resulting product was recrystallized twice from methanol (35% overall yield, 300° C.). $^1$H NMR (400 MHz, DMSO-d$_6$) δ: 8.83 (d, J=6 Hz, 4H), 8.62 (s, 2H), 8.23 (d, J=12.4 Hz, 2H), 8.20 (d, J=4.4 Hz, 4H), 7.96 (d, J=8.4 Hz, 2H), 7.82 (d, J=8.4 Hz, 2H), 7.57 (d, J=15.6 Hz, 2H), 4.52 (t, 2H), 4.25 (s, 6H), 2.94 (s, 3H), 2.25 (t, 4H), 2.21 (t, 2H), 1.84 (m, 4H), 1.53 (m, 4H), 1.48 (m, 2H). EA (C$_{38}$H$_{45}$I$_3$N$_4$.0.5H$_2$O): calc (obs %) C, 48.17 (48.03); H, 4.89 (4.91); N, 5.91 (5.86).

EXAMPLE 2

Preparation of Compound 2

The compound was prepared in a manner similar to that described in Example 1.

Overall yield: 28%, mp>300° C. $^1$H NMR (400 MHz, DMSO-d$_6$) δ: 8.80 (d, J=6 Hz, 4H), 8.62 (s, 2H), 8.23 (d, J=16 Hz, 2H), 8.20 (d, J=4.4 Hz, 4H), 7.93 (d, J=8.8 Hz, 2H), 7.80 (d, J=8.4 Hz, 2H), 7.53 (d, J=16 Hz, 2H), 4.52 (t, 2H), 4.25 (s, 6H), 3.26 (m, 6H), 1.89 (m, 2H), 1.73 (m, 6H), 1.51 (m, 2H), 1.34 (m, 2H). EA (C$_{39}$H$_{47}$I$_3$N$_4$.0.5H$_2$O): calc (obs %) C, 48.72 (48.59); H, 5.03 (5.02); N, 5.83 (5.75).

EXAMPLE 3

Preparation of Compound 3

The compound was prepared in a manner similar to that described in Example 1.

Overall yield: 31%, mp>300° C. $^1$H NMR (400 MHz, DMSO-d$_6$) δ: 8.82 (d, J=6.4 Hz, 4H), 8.63 (s, 2H), 8.20 (d, J=6.4 Hz, 4H), 8.19 (d, J=16 Hz, 2H), 7.92 (d, J=8.4 Hz, 2H), 7.77 (d, J=8.4 Hz, 2H), 7.55 (d, J=16 Hz, 2H) 4.48 (t, 2H), 4.24 (s, 6H), 3.25 (m, 6H), 2.94 (s, 3H), 1.80 (m, 2H), 1.73 (m, 4H), 1.59 (m, 2H), 1.50 (m, 2H), 1.30 (m, 4H), 1.24 (m, 4H). EA (C$_{42}$H$_{53}$I$_3$N$_4$.H$_2$O): calc (obs %) C, 49.82 (49.73); H, 5.47 (5.43); N, 5.53 (5.45).

EXAMPLE 4

Preparation of Compound 4

The compound was prepared in a manner similar to that described in Example 1.

Overall yield: 30%, mp>300° C. $^1$H NMR (400 MHz, DMSO-d$_6$) δ: 8.81 (d, J=6.0 Hz, 4H), 8.67 (s, 2H), 8.22 (d, J=6.4 Hz, 4H), 8.20 (d, J=16 Hz, 2H), 7.92 (d, J=8.4 Hz, 2H), 7.76 (d, J=8.8 Hz, 2H), 7.58 (d, J=16 Hz, 2H), 4.47 (t, 2H), 4.25 (s, 6H), 3.28 (m, 6H), 2.95 (s, 3H), 1.75 (m, 4H), 1.59 (m, 4H), 1.21 (m, 12H). EA (C$_{43}$H$_{55}$I$_3$N$_4$.1.5H$_2$O): calc (obs %) C, 49.87 (49.79); H, 5.64 (5.62); N, 5.41 (5.35).

EXAMPLE 5

Preparation of Compound 5

The compound was prepared in a manner similar to that described in Example 1.

Overall yield: 31%, mp>300° C. $^1$H NMR (400 MHz, DMSO-d$_6$) δ: 8.81 (d, J=6.8 Hz, 4H), 8.65 (s, 2H), 8.24 (d, J=16 Hz, 2H), 8.20 (d, J=7.2 Hz, 4H), 7.92 (d, J=8.8 Hz, 2H), 7.76 (d, J=8.8 Hz, 2H), 7.56 (d, J=16 Hz, 2H), 4.45 (t, 2H), 4.29 (s, 6H), 3.25 (m, 6H), 2.95 (s, 3H), 1.75 (m, 6H), 1.61 (m, 2H), 1.525 (m, 2H), 1.202 (m, 16H). EA (C$_{46}$H$_{61}$I$_3$N$_4$.H$_2$O): calc (obs %) C, 51.70 (51.61); H, 5.94 (5.91); N, 5.24 (5.17).

EXAMPLE 6

Preparation of Compound 6

Compound 6 was prepared in a manner similar to that described in Example 1, using 3,6,9-trioxaundecane-1,1'-dibromide, which was prepared according to Soma et al., *J. Phys. Chem. B*, 1998, 102, 6152-6160.

Overall yield: 24%, mp>300° C. $^1$H NMR (400 MHz, DMSO-d$_6$) δ: 8.80 (d, J=6 Hz, 4H), 8.68 (s, 2H), 8.23 (d, J=16 Hz, 2H), 8.20 (d, J=7.2 Hz, 4H), 7.90 (d, J=8.8 Hz, 2H), 7.76 (d, J=8.4 Hz, 2H), 7.59 (d, J=16 Hz, 2H), 4.64 (t, 2H), 4.24 (s, 6H), 3.82 (t, 2H), 3.71 (t, 2H), 3.47 (m, 4H), 3.38 (m, 10H), 2.97 (s, 3H), 1.67 (m, 4H), 1.43 (m, 2H). EA (C$_{42}$H$_{53}$I$_3$N$_4$O$_3$.2H$_2$O): calc (obs %) C, 46.77 (46.68); H, 5.33 (5.31); N, 5.19 (5.12).

EXAMPLE 7

Preparation of Compound 7

The compound was prepared in a manner similar to that described in Example 1.

Overall yield: 27%, mp>300° C. $^1$H NMR (400 MHz, DMSO-d$_6$) δ: 8.94 (s, 2H), 8.87 (d, J=6.4 Hz, 2H), 8.56 (d, J=8.4 Hz, 2H), 8.46 (t, J=8 Hz, 2H), 8.16 (d, J=16 Hz, 2H), 8.03 (d, J=8.8 Hz, 2H), 7.87 (t, 2H), 7.86 (d, J=8.4 Hz, 2H), 7.67 (d, J=16 Hz, 2H), 4.55 (t, 2H), 4.45 (s, 6H), 3.37 (m, 6H), 2.99 (s, 3H), 1.85 (m, 4H), 1.77 (m, 4H), 1.52 (m, 2H). EA (C$_{38}$H$_{45}$I$_3$N$_4$.0.5H$_2$O): calc (obs %) C, 48.17 (48.09); H, 4.89 (4.86); N, 5.91 (5.88).

EXAMPLE 8

Binding Between Carbazole Compounds and Linear Duplex DNA

Compounds 3, 4, 6, and 7 were tested for their binding to linear duplex DNA (LD) following the method described in US 2005/0249669 and U.S. Pat. No. 6,979,738. The sequence of LD is:

```
LD:    5'-GCGCAATTGCGC-3'      (SEQ ID NO: 1)
```

The results of the absorption spectra of compounds 3, 4, 6, and 7 showed a red shift of the absorption band and a decrease of the molar absorption coefficient. These changes indicate that these compounds bind to LD. The fluorescence spectra of compounds 3, 4, 6, and 7 showed that upon interaction with DNA their fluorescence is enhanced by at least one order of magnitude.

EXAMPLE 9

Cancer Cell Diagnosis

Compounds 1-7 were tested for their efficacy in differentiating CL1-0 lung cancer cells from MRC-5 human lung normal fibroblast cells by flow cytometry. The mean fluorescence of compounds 1-7 was unexpectedly stronger in cancer cells than in normal cells. Compound 3 displayed the strongest difference between cancer cells and normal cells.

The fluorescence intensity of 3,6-bis(1-methyl-4-vinylpyridinium)carbazole diiode (BMVC) described in Kang et al., *J. Chin. Chem. Soc.*, 2005, 52, 1069-1072 and Compound 3 were measured in CL1-0 lung cancer cells and MRC-5 human lung normal fibroblast cells as a function of incubation time. It was found in this study that the fluorescence of Compound 3 in cancer cells was about three times stronger than that of BMVC, while both compounds displayed weak fluorescence in normal cells.

In addition, the efficacy of Compound 3 in differentiating CL1-0 lung cancer cells from MRC-5 human lung normal fibroblast cells was also tested using the device described in US 2007/0098233 and Kang et al., *Analyst*, 2007, 132, 745-749. The fluorescence of Compound 3 was found to be significantly stronger in cancer cells than in normal cells.

EXAMPLE 10

Lipophilicity

The lipophilicity of compounds 1-6 was determined by the logarithm of the n-octanol/water coefficient as described in Engelmann et al., *Int. J. Pharm.*, 2007, 329, 12-18. Compounds 1-6 had a log P value between −1.7 and −2.4, indicating that the compounds displayed different degrees of lipophilicity.

EXAMPLE 11

Intracellular Localization

For cellular localization studies, CL1-0 lung cancer cells were plated on cover slips in 12-well plates for 24 h. After 24 hr incubation with 1 or 5 μM of compounds 1-7, 50 nM Mitotracker red CMXRos (M-7512, Invitrogen) was added to the cells for 30 min. 40 nM Hoechst 33342 (Sigma) was then added to the cells for 10 min and the cells were washed twice with PBS. The cells were visualized with a confocal microscope (Leica TCS SP5) at the National Taiwan University Hospital. The regions of overlap between the fluorescent compounds 1-7 and Mitotracker red were determined with a MetaMorph offline 7.6 software program. The results showed that compounds with higher lipophilicity were excluded from the nucleus of the cancer cells and localized in the mitochondria, which were stained by Mitotracker red.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the carbazole compounds described above can also be made, screened for the above-described activities and used to practice this invention. Thus, other embodiments are also within the claims.

What is claimed is:

1. A compound of formula (I):

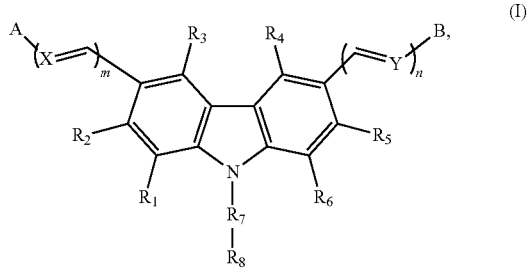

wherein
each of A and B, independently, is heteroaryl containing at least one nitrogen atom;
each of X and Y, independently, is CH or N;
each of $R_1$-$R_6$ is H;
$R_7$ is $C_2$-$C_{16}$ alkyl, $C_2$-$C_{16}$ alkenyl, or $C_2H_4$—$(ZC_2H_4)_v$—, Z being O, S, or Se and v being 1, 2, or 3;
$R_8$ is $C_3$-$C_8$ heterocycloalkyl containing a nitrogen atom, $C_3$-$C_8$ heterocycloalkyl substituted by an amino group, or $C_3$-$C_8$ cycloalkyl substituted by an amino group; and
each of m and n, independently, is 1, 2, or 3.

2. The compound of claim 1, wherein each of A and B, independently, is heteroaryl containing one or two nitrogen atoms.

3. The compound of claim 1, wherein each of A and B, independently, is substituted by $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, $C_1$-$C_6$ alkoxy, $C_1$-$C_6$ alkylamino, or $C_1$-$C_6$ dialkylamino.

4. The compound of claim 2, wherein each of m and n is 1.

5. The compound of claim 4, wherein each of X and Y is CH.

6. The compound of claim 1, wherein $R_7$ is $C_8$-$C_{12}$ alkyl, $C_8$-$C_{12}$ alkenyl, $C_8$-$C_{12}$ alkynyl, or —$C_2H_4$—$(ZC_2H_4)_v$—, Z being O, S, or Se and v being 1, 2, or 3.

7. The compound of claim 6, wherein each of A and B, independently, is heteroaryl containing one or two nitrogen atoms.

8. The compound of claim 7, wherein each of m and n is 1.

9. The compound of claim 8, wherein each of X and Y is CH.

10. The compound of claim 9, wherein $R_8$ is heterocycloalkyl containing a nitrogen atom, which is optionally positively charged.
11. The compound of claim 10, wherein each of A and B is 1-methyl-pyridinium-4-yl and $R_8$ is 1-methyl-piperidinium-1-yl.
12. The compound of claim 5, wherein the compound is any of the following compounds:
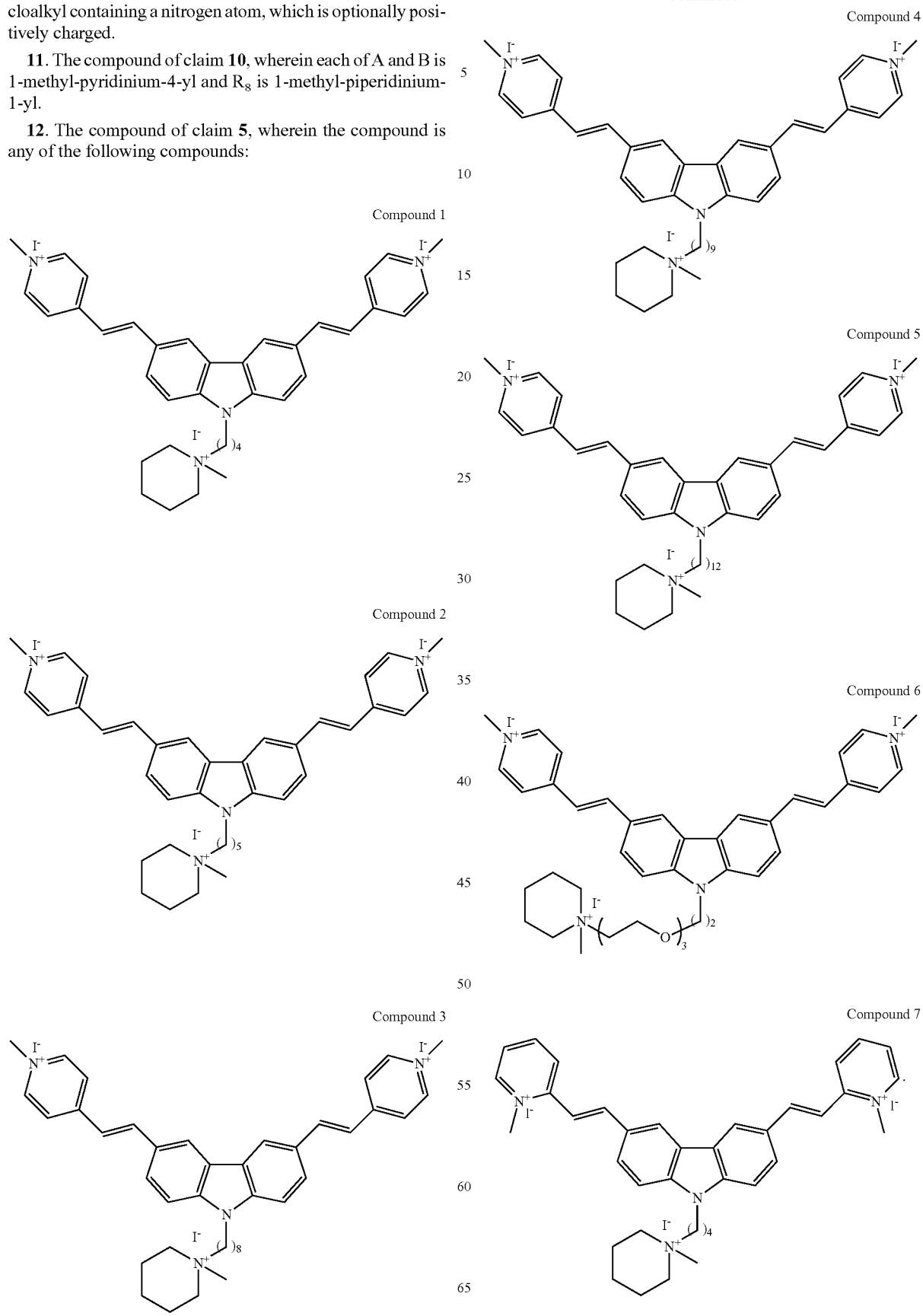

13. A method for detecting a cancer cell, comprising:
contacting cells in a sample with a compound of formula (I):

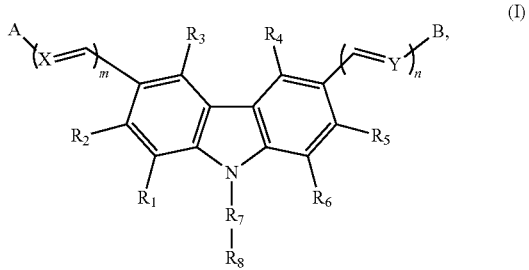

in which
- each of A and B, independently, is heteroaryl containing at least one nitrogen atom;
- each of X and Y, independently, is CH or N;
- each of $R_1$-$R_6$ is H;
- $R_7$ is $C_2$-$C_{16}$ alkyl, $C_2$-$C_{16}$ alkenyl, $C_2$-$C_{16}$ alkynyl, or —$C_2H_4$—$(ZC_2H_4)_v$—, Z being O, S, or Se and v being 1, 2, or 3;
- $R_8$ is $C_3$-$C_8$ heterocycloalkyl containing a nitrogen atom, $C_3$-$C_8$ heterocycloalkyl substituted by an amino group, or $C_3$-$C_8$ cycloalkyl substituted by an amino group; and
- each of m and n, independently, is 1, 2, or 3;

detecting fluorescence emission from the cells; and
determining whether the sample contains a cancer cell based on the intensity of the fluorescence;
wherein a greater fluorescent intensity, relative to that obtained from a cancer cell-free sample, indicates that the sample contains a cancer cell.

14. The method of claim 13, wherein each of A and B, independently, is heteroaryl containing one or two nitrogen atoms.

15. The method of claim 14, wherein each of A and B, independently, is substituted by $C_1$-$C_8$ alkyl, $C_2$-$C_8$ alkenyl, $C_2$-$C_8$ alkynyl, $C_3$-$C_8$ cycloalkyl, $C_3$-$C_8$ heterocycloalkyl, $C_1$-$C_6$ alkoxy, $C_1$-$C_6$ alkylamino, or $C_1$-$C_6$ dialkylamino.

16. The method of claim 15, wherein each of m and n is 1.

17. The method of claim 16, wherein each of X and Y is CH.

18. The method of claim 13, wherein $R_7$ is $C_8$-$C_{12}$ alkyl, $C_8$-$C_{12}$ alkenyl, $C_8$-$C_{12}$ alkynyl, or —$C_2H_4$—$(ZC_2H_4)_v$—, Z being O, S, or Se and v being 1, 2, or 3.

19. The method of claim 13, wherein the compound is a compound of claim 12.

20. The method of claim 13, wherein the sample is obtained from a patient suspected of having cancer.

21. The compound of claim 1, wherein each of A and B, independently, is heteroaryl containing one or two nitrogen atoms; $R_7$ is $C_2$-$C_{16}$ alkyl; $R_8$ is heterocycloalkyl containing a nitrogen atom, optionally positively charged; each of X and Y is CH; and each of m and n is 1.

22. The compound of claim 4, wherein $R_7$ is $C_8$-$C_{12}$ alkyl and $R_8$ is heterocycloalkyl containing a nitrogen atom, optionally positively charged.

* * * * *